(12) United States Patent
Hamunen

(10) Patent No.: US 7,202,372 B2
(45) Date of Patent: Apr. 10, 2007

(54) PROCESS FOR THE ISOLATION OF STEROLS AND/OR WAX ALCOHOLS FROM TALL OIL PRODUCTS

(75) Inventor: Antti Hamunen, Raisio (FI)

(73) Assignee: Sterol Technologies, Ltd., Raisio (FI)

( * ) Notice: Subject to any disclaimer, the term of this patent is extended or adjusted under 35 U.S.C. 154(b) by 402 days.

(21) Appl. No.: 10/487,937

(22) PCT Filed: Sep. 6, 2002

(86) PCT No.: PCT/FI02/00718

§ 371 (c)(1),
(2), (4) Date: Sep. 1, 2004

(87) PCT Pub. No.: WO03/022865

PCT Pub. Date: Mar. 20, 2003

(65) Prior Publication Data

US 2005/0010061 A1    Jan. 13, 2005

(30) Foreign Application Priority Data

Sep. 7, 2001   (EP) .................. 01660162

(51) Int. Cl.
*C07J 9/00*   (2006.01)
(52) U.S. Cl. ............... 552/540; 552/545; 549/413
(58) Field of Classification Search ............... 552/540, 552/545; 549/413
See application file for complete search history.

(56) References Cited

U.S. PATENT DOCUMENTS

| | | | |
|---|---|---|---|
| 3,887,537 A | 6/1975 | Harada et al. | |
| 4,148,810 A | 4/1979 | Struve | |
| 4,151,160 A | 4/1979 | Koebner | |
| 4,374,776 A | 2/1983 | Struve et al. | |
| 4,483,791 A | 11/1984 | Phillips, Jr. | |
| 5,627,289 A | 5/1997 | Jeromin et al. | |
| 5,670,669 A | 9/1997 | Hunt | |

FOREIGN PATENT DOCUMENTS

| | | |
|---|---|---|
| EP | 0 952 208 A | 10/1999 |
| EP | 0 952 208 A2 | 10/1999 |
| WO | 99/16785 | 4/1999 |
| WO | 99 42471 A1 | 8/1999 |

OTHER PUBLICATIONS

WO 99 42471 A published Aug. 26, 1999.
Database WPI Section Ch, Week 198617 Derwent Publications Ltd., London, GB; Class B01, AN 1986-109257 & JP 61 050996 A, Mar. 13, 1986.
XP-002190899.
European Search Report, EP 01 66 0162.

*Primary Examiner*—Kamal A. Saeed
*Assistant Examiner*—Rei-tsang Shiao
(74) *Attorney, Agent, or Firm*—Arent Fox LLP

(57) ABSTRACT

The invention relates to a process for recovering sterols and/or wax alcohols from a crude tall oil based source material comprising sterols and/or wax alcohols in esterified form and fatty and/or rosin acids and optionally sterols and/or wax alcohols in free form, said method comprising the steps of: a) converting free acids in the source material to corresponding salts, b) removing water if present, c) transesterifying the esterified sterols and/or wax alcohols present in the dry material obtained in step a or step b to liberate sterols and/or wax alcohols, d) evaporative fractionating the transesterified material, and e) isolating sterols and/or wax alcohols from the obtained fraction(s) and/or the residue.

13 Claims, No Drawings

PROCESS FOR THE ISOLATION OF STEROLS AND/OR WAX ALCOHOLS FROM TALL OIL PRODUCTS

CROSS-REFERENCE TO RELATED APPLICATION

This application is a National Stage entry of International Application No. PCT/FI02/00718, filed Sep. 6, 2002, the entire specification claims and drawings of which are incorporated herewith by reference.

The invention relates to an improved process for the separation of saponifiable and/or unsaponifiable substances from materials containing fatty and/or rosin acid esters of alcohols such as, for example esters of sterols and/or wax alcohols. Especially the invention is suitable for separation of sterols from tall oil pitch or crude tall oil.

Tall oil pitch is the distillation residue of crude tall oil, which is made by acidulation of crude sulphate soap which is the fraction containing wood extractives formed during wood pulping processes. Typically crude tall oil contains sterols 3–7 weight-% and a couple of percent wax alcohols. During distillation of crude tall oil to tall oil most of the sterols and wax alcohols will remain in the tall oil pitch fraction. The sterol content of tall oil pitch varies depending on the distillation profile and quality of the crude tall oil and is typically between 8 and 16 weight-%. Usually well over 50% of the sterols and other wood derived alcohols are esterified with fatty acids in tall oil pitch, and in crude tall oil such esters are formed e.g. during storage, or during handling at elevated temperatures.

Sterols and/or wax alcohols are the main components to be separated according to the invention. They are hereafter referred to as valuable substances.

Some of the known processes concentrate the valuable substances in question by using solvent extraction processes, taking advantage of the difference of solubility between unsaponifiable substances and the soap matrix. Prior to extraction the valuable substances have been liberated from the esters—in which form they in large extent exist in the source materials—by saponification with alkali metal hydroxides. In the saponification the free acids and acid part of the esters form the soap, i.e. salts of the organic acids present. However, it has been noticed that it is often difficult to further purify the valuable substances like sterols to desired high purity degrees from the extracts without extensive fractionation by e.g. distillation. When combining expensive extraction steps with evaporation fractionation, the investments and operation costs of the separation processes become very expensive. The purpose of this invention is to simplify the processes and make them thereby also cheaper to use and still obtain a very pure product.

In case the valuable substances are separated directly from the saponified soap materials by distillation, the difference between the boiling point of volatile products, such as unsaponifiable substances, and the boiling point of different organic acid soaps is so remarkable that separation is possible to perform at a high efficiency. However, a problem related to this separation technique is the very high melting point of the sodium or potassium soaps (i.e. the sodium or potassium salts of fatty acids, rosin acids etc.) which remain in the distillation residues. Even when melted, these soaps form extremely viscous liquids, which make industrial handling difficult. While it is necessary to maintain the fluidity of the soap residue a high temperature e.g. above 200° C. is needed, and therefore there is a risk that the valuable substances are decomposed compromising the yield and the quality of the final product.

U.S. Pat. No. 3,887,537 discloses a process for recovering besides sterols also fatty acids and rosin acids from tall oil pitch by saponifying the tall oil pitch with an alkali metal hydroxide (sodium hydroxide) in the presence of an alkanol (such as butanol) to soaps and unsaponifiables, and then feeding the mixture into a thin film evaporator to evaporate and remove the low-boiling matter including light unsaponifiables, water and alkanol. Subsequently the bottom fraction is fed into a second thin film evaporator for removing unsaponified heavy material including sterols. Finally, the bottom soap fraction from the second evaporator is acidulated with a mineral acid to obtain fatty acids and rosin acids. One of the difficulties of this process is that the soaps are very viscous making the handling of these soaps troublesome.

WO 99/16785 discloses a method for separating unsaponifiable material from tall oil pitch by saponifying the pitch with a mixture of sodium hydroxide and potassium hydroxide to form sodium and potassium salts of fatty acids and rosin acids, and then evaporating the unsaponifiable material containing sterols using a thin film evaporator. The unevaporated portion of the pitch which comprises sodium and potassium salts of the saponifiable material is acidulated to generate the rosin and fatty acids. Also this method suffers from the difficult material handling of the sodium and/or potassium soaps.

WO 99/42471 discloses a method of separating sterols from tall oil pitch by saponifying the tall oil pitch with an alkali metal base comprising sodium hydroxide, potassium hydroxide or a mixture thereof, followed by neutralising the saponified pitch with an acid and heating the neutralised pitch to remove water. The thus obtained modified pitch containing free sterols is subjected to evaporation to remove light ends and then the bottom fraction from the evaporation is evaporated using a wiped evaporator to produce a light phase distillate containing free sterols. Subsequently the light phase distillate is dissolved in a solvent comprising an alcohol, and the free sterols are crystallised from the solution by cooling. A disadvantage of this method is that the yield of sterols is rather low.

U.S. Pat. No. 4,151,160 discloses a process for the separation of fatty acids from the unsaponfiable constituents contained in a head fraction of tall oil by converting the fatty acids into their zinc or lead soaps, and then removing the unsaponifiable constituents by vacuum distillation. Subsequently the non-volatile metal soaps remaining as distillation residue are acidulated to produce the desired fatty acids. Typical components of the light boiling unsaponifiables are lower terpenes and rosin degradation products, and these products have minor commercial value. The content of sterols in the tall oil heads is very low, considerably below 1% by weight, and thus the tall oil head fraction is not suitable as a source for the production of sterols.

U.S. Pat. No. 4,483,791 discloses a process for the recovery of fatty acids from tall oil heads by converting the fatty acids contained in the tall oil heads into a mixture of magnesium soap and sodium soap, and then vacuum stripping the reaction product. Finally the soaps are acidulated to produce the desired fatty acids.

EP 952 208 discloses a process for the separation of unsaponifiables from black-liquor soaps or tall oil by dehydrating the raw material, melting and distillation in a short path evaporation column. This publication also suggests the addition of unsaponifiables to soap or neutralised tall oil before the drying step in order to reduce the necessary temperature to maintain the mixture at a state of adequate fluidity during the drying process. These added unsaponifiables comprise recirculated unsaponifiables from the process which unsaponifiables are low boiling substances. These recirculated unsaponifiables have a favourable effect on the drying but are believed to have a disadvantageous effect on the subsequent distillation step as the low boiling unsaponifiables are evaporated together with the sterol fraction resulting in a dilution of the sterol fraction and because they do not remain in the residue fraction they cannot facilitate handling of the residue through viscosity reducing effect as in the case if they were present in the residue.

In U.S. Pat. No. 4,148,810 sterols are separated from deodorizer distillates formed during edible oil refining by liberating the sterols from the fatty acid esters and forming fatty acid alkyl esters using transesterification with a lower alkanol catalysed by small amounts of alkaline compounds. The amount of alkaline catalyst e.g. NaOMe used is stoichiometrically much smaller than the acidic groups present in the source materials. This means that actually, when these catalysts have been used, they form acid salts, which actually act as catalyst (not the alkalis themselves). Acid salts are much weaker catalysts than clearly alkaline compounds and for that reason the reaction conditions which have to be applied are severe: temperature preferably 200–220° C. for several hours. As a consequence of the high temperature and long residence time in practice a considerable part of the sterol content will be thermally destroyed during the process. After the transesterification sterols are isolated by dissolving the mixture in an aprotic solvent and forming a sterol adduct with $CaCl_2$, which was isolated and decomposed to free sterol. U.S. Pat. No. 4,374,776 discloses a similar process which differs only in that a sterol concentrate is isolated using molecular distillation instead of the adduct formation step in U.S. Pat. No. 4,148,810.

U.S. Pat. No. 5,627,289 discloses a method for isolating sterols and tocopherol from fatty acids in deodorizers distillate comprising esterification of free fatty acids with methanol using an acid catalyst, transesterification using methanol in the presence of a basic catalyst and distillation to remove fatty acid methyl esters and obtain a mixture containing sterols and tocopherol. In U.S. Pat. No. 5,670,669 the esterification of deodorizers distillate is performed using either fatty alcohols or methanol whereafter transesterification is performed. After that the fatty acid esters are distilled off, and tocopherol and sterols are separated using a solvent mixture forming two separate phases. In these publications the problem of acidic groups in the source material prior to the transesterification step is solved by acid catalysed esterification of the organic acids. However, due to the several neutralisations when changing catalyst systems, solvent removal and drying steps the overall process becomes relatively complicated.

The process of the present invention has solved the problems related to prior known evaporation processes for separating sterols and other valuable substances from materials containing the valuable substances in esterified form i.e. from crude tall oil source material such as from crude tall oil and tall oil pitch, preferably from tall oil pitch, by converting the free fatty and/or rosin acids to salts, transesterifying the acid parts of the esters, i.e. fatty and/or rosin acids, into esters of aliphatic lower alcohols, preferably lower alcohols C1–6, such as methanol and ethanol, and performing an evaporative fractionation of the material after this transesterification process.

As mentioned above sterols and/or wax alcohols are the main components to be separated by the process of the present invention. However, the present invention is not restricted to the separation of these components only. Depending on the quality of the raw material used, it is also possible to separate other components. These components include for example the alcohol esters of fatty and/or rosin acids formed in the transesterification and fatty and/or rosin acids obtainable from the salt as well as components included in light distillate fractions of tall oil pitch or crude tall oil (e.g. stilbene compounds).

The invention especially relates to separation of the mentioned valuable substances including sterols and/or wax alcohols by means of neutralising tall oil pitch or crude tall oil, i.e. converting free acids in the pitch or crude tall oil to salts whereby the esterified acids mainly remain unhydrolysed, liberating the valuable substances by transesterification, performing an evaporation fractionation and finally isolating the valuable substances.

Thus, the present invention provides a process for recovering sterols and/or wax alcohols from a crude tall oil based source material comprising sterols and/or wax alcohols in esterified form and fatty and/or rosin acids and optionally sterols and/or wax alcohols in free form, said method comprising the steps of:

a) converting free acids in the source material to corresponding salts, b) removing water if present, c) transesterifying the esterified sterols and/or wax alcohols present in the dry material obtained in step a or step b to liberate sterols and/or wax alcohols, d) evaporative fractionating the transesterified material, and e) isolating sterols and/or wax alcohols from the obtained fraction(s) and/or the residue.

The conversion step a is preferably performed using an oxide, hydroxide or alkoxide of an alkali metal or alkaline earth metal.

The transesterification step c is preferably an alkaline catalysed transesterification wherein the catalyst preferably comprises an alkoxide or hydroxide of an alkali metal.

The transesterification step c can be performed using a lower alcohol as alcohol reagent.

The transesterification step c can also be performed using a high boiling polyhydric alcohol such as ethylene glycol, propylene glycol, glycerol or diethylene glycol as alcohol reagent.

The boiling point of the high boiling polyhydric alcohol is preferably at least 120° C.

In the transesterification the reaction temperature can be from at least 80° C., preferably from about 140° C. to about 170° C., more preferably from about 150° C. to about 160° C.

If a lower alcohol is used in excess as alcohol reagent in the transesterification step c, the fractionation step d preferably includes the steps of d1) evaporation of excess of lower alcohol reagent partly or completely, and d2) evaporation fractionation of the transesterified material.

According to the invention the organic salts formed during conversion step a can after the transesterification step c be completely or partially acidulated to corresponding acids before performing fractionation step d.

According to the invention the acids present in the source material can be partially esterified before performing conversion step a. This esterification can be performed using a lower alcohol or a high boiling polyhydric alcohol such as ethylene glycol, propylene glycol, glycerol or diethylene glycol as alcohol reagent.

Furthermore, step a and step c can be performed in the same stage under anhydrous conditions using an alkoxide of an alkali metal or alkaline earth metal such as sodium methoxide as reagent in the conversion step a and as catalyst in the transesterification step c.

"Lower alcohol" means an alcohol having 1 to 6 carbon atoms, preferably 1 to 4 carbon atoms. Preferred lower alcohols are methanol and ethanol.

In the process according to the present invention the problems involved in the prior art utilising transesterification are solved by converting the free acids to salts and excluding any moisture possibly present in the material before the transesterification which preferably is alkali catalysed. Because the acid value of the source material in question is relatively low compared to the saponification value, the amount of organic acid salts formed upon the conversion is generally so low that this material does not interfere too much the evaporative fractionation in the later stages of the overall process.

If, however, the acid value of the source material is so high that handling problems due to the salts formed on the conversion can be expected to occur in the later process stages, the material can be partially esterified prior to the conversion and transesterification. Otherwise the process steps are the same for this embodiment. For this esterification any alcohol can be used e.g. lower alcohols, but it is advantageous to use high boiling alcohols with high hydroxyl density i.e. polyhydric alcohols (e.g. ethylene or propylene glycol, glycerol or diethylene glycol) as the alcohol reagent, because: a) water formed in the esterification can be evaporated from the reaction medium which facilitates completion of the reaction and no need of evaporation of the excess reagent before transesterification is needed, b) for the purpose to lower the acid value only small amounts of alcohol are needed, c) optionally these high boiling polyhydric alcohols can be used also as reagents in the transesterification stage (instead of lower alcohol, e.g. methanol) and due to their water solubility, can be recovered from the fractions formed during evaporative fractionation by water washes (after optional splitting of the esters of these alcohols, if complete recovery of these alcohols is desired). Any known catalyst used for esterification of acids and alcohols can be used for this esterification. Examples of possible catalysts include mineral acids, toluene and methane sulfonic acids, acidic ion exchange resins, salts or oxides of metals (e.g. ZnO). Preferably a mineral acid may be used. In the esterification reaction the temperature may be at least 80° C., preferably from about 80° C. to about 200° C. The formed water is preferably removed at normal or reduced pressure by evaporation.

In the first step of the process according to the present invention the free acids of the source material or the free acids remaining after the esterification are first converted to salts by using oxides or hydroxides of alkali metals or alkaline earth metals, or with respective metal alkoxides. If the conversion is done by using a reagent which does not produce water or consumes it when used sufficiently (alkoxides, metal oxides), the dry reagent is conveniently added into the source material as dissolved or slurried into dry alcohol—preferably methanol—used in the transesterification. On the other hand, if, for example, sodium hydroxide is used for the conversion reaction, it can be dosed as water solution and all the water has then to be removed before starting the transesterification.

In the process according to the invention it is important also to take care of that no water is present during the alkaline catalysed transesterification step, because the water would prevent the transesterification reaction. This means that the mixture must be dried before transesterification if the conversion of free acids to salts has been made by using reagents producing water. This drying can be performed by simple evaporation, azeotropic distillation or by adding components, which react with water. Examples of suitable dessicants for the drying are metal alkoxides, which then can be used also to catalyse the transesterification reaction itself.

The transesterification reaction is an equilibrium reaction. When a low molecular weight alcohol is used for the reaction, it is in practice impossible to run the reaction into completion by removing reaction products from the system. Therefore it is important to use stoichiometric excess of the alcohol reagents for the reaction. When the excess of lower alcohol used in the transesterification reaction is high enough, and the process conditions favourable, only very small amounts of original esters of valuable sterols or other valuable alcohols can be detected after the reaction. For example, in typical cases, when the source material is tall oil pitch, suitable reaction conditions are ratio of methanol:tall oil pitch (dry weight) at least 0.2:1, preferably about 1:1 (which corresponds to the molar ratio MeOH:sterols of about 100), reaction temperature about 150–160° C., catalyst NaOMe (0,3–0,5 weight-% of the dry pitch), and reaction time about 1–3 h.

The transesterification can be performed using an alkali like an alkoxide or hydroxide of an alkali metal. Most preferably an alkali metal alkoxide such as alkali metal methylate or ethylate is used e.g. sodium or potassium methylate (NaOMe or KOMe).

A preferred embodiment of the invention is to use an alkaline alkoxide, preferably an alkali metal alkoxide e.g. NaOMe as reagent in the conversion step a and as catalyst in the transesterification step c both steps being performed in one reaction without any formation of water, and therefore there is no need for the step including removal of water. Water, if present from the preceding processing steps, should though have been removed before starting the conversion. It is to be noted that if an alkali metal alkoxide is used both as a reagent for the conversion and as a catalyst in the transesterification the totally added molar amount of alkali metal alkoxide should be more than the molar amount of free acids. Preferably the amount of alkali metal alkoxide should be equal to the molar amount of acids added by a catalytic amount of the chemical. The catalytic amount may be e.g. at least 0.005 weight-% of the solids of the crude tall oil based source material, preferably between 0.05–0,2 weight-%. It has also been noticed that the acid value of the crude tall oil based source material in this embodiment should be at least 2.5, preferably at least 5 mg KOH/g dry weight, before adding alkali metal alkoxide to obtain a relevant formation of salts in the conversion.

In principle it is possible to also make the transesterification as an acid catalysed reaction, whereby no conversion of free acids or drying is needed, but it has been noticed that reaction rates are very slow compared to alkaline transesterification. Hence the reaction conditions usually must be so severe in an acid catalysed reaction that losses of the valuable substances through degradation reactions may occur as well.

In another embodiment of the invention the transesterification can also be performed using high boiling polyhydric alcohols. Preferred alcohols are e.g. ethylene glycol, propylene glycol, glycerol and diethylene glycol. An advantage of using these alcohols is that the transesterification can be performed also at normal pressure. The behaviour in the evaporative fractionation may also sometimes be beneficial. Especially, the removal of water by distillation done before the transesterification is much easier to realise because of the higher boiling point of these alcohols. Some of the excess of alcohol may also be incorporated into the fractions obtained in the evaporation fractionation.

After alkali catalysed transesterification the reaction mixture, in addition to excessive alcohol used in the reaction, contains carboxylic acid salts which are formed from fatty and/or rosin acids during the conversion, acids which are esterified with the alcohol reagent used and unsaponifiable valuable substances including sterols and other higher alcohols in free form.

The next steps in the overall process include the removal of excess solvent partly or completely (i.e. alcohol used in the transesterification) and the evaporative fractionation of the reaction mixture in order to remove the components which disturb the final purification steps of valuable substances. Removal of the solvent, which also is an evaporative process can be performed using any evaporative processes or their combinations such as flashing, falling film evaporations, distillation at normal or reduced pressure, thin film evaporation. If needed, the alcohol can be removed partly or totally also before the possible acidulating step described beneath.

In the succeeding evaporative fractionation steps the acid salts are nonvolatile and remain in the distillation residues. In typical cases the acid value of tall oil pitch is 15–50 mg KOH/g dry weight and only this portion is converted into nonvolatile salts, whereas the acids in ester form (saponification number typically 80–150 mg KOH/g dry weight pitch) have been transformed into volatile alkyl esters. The advantage of the present invention compared to prior art regarding tall oil pitch is, that the amount of these nonvolatile high viscous high melting components is much smaller than in the conventional methods where all the esters and acids of the source material are saponified with alkali. This small amount of acid salts does not normally cause impassable handling problems during the evaporative fractionation. However, if the melting and viscosity behaviour of the residues cause problems during the evaporation processes, it is possible to completely or partially acidulate the salts before the evaporative fractionation with e.g. mineral acid or using cation exchange resin and so liberate organic acids (i.e. fatty and/or rosin acids) from their salts and thereby make them volatile. This may be done after the alkaline catalysed transesterification. These acids can even be esterified in an acid catalysed reaction e.g. with the lower alcohol used as the alcohol reagent in the transesterification. The esterification can be performed by using as catalyst a mineral acid, a toluene or methane sulfonic acid, acidic anion exchange resin or a salt or oxide of a metal e.g. ZnO. This esterification reaction can be performed in an autoclave at a temperature of at least 80° C. In this case the organic acids will also become volatile and can be separated from the higher molecular weight valuable sterols and other higher molecular weight substances in the evaporation stage into the light distillate fractions. When necessary the mixture can be washed with water after such an acidulation process in order to remove for example the inorganic salts formed during the acidulation. The water wash can be performed before the evaporation fractionation step or preferably after having evaporated the excess of lower alcohol reagent from the mixture i.e. after step d1.

If such an acidulation step is included into the overall process the pH of the reaction mixture should not be allowed to drop too low—it should be kept above 3,5–4—in order to avoid possible re-esterification reactions during the subsequent evaporative fractionation.

In the following disclosure of the evaporation fractionation process special attention will be paid to the cases where the aim is to separate sterols and/or wax alcohols as valuable substances.

The evaporative fractionation can be performed according to several alternative strategies. In one embodiment (A) the light fraction is first distilled preferably by using short path or thin film evaporation and then the valuable substances are recovered from the residue by using other separation techniques either after further high vacuum fractionation or from the residue as such. Short path distillation means that the condensation of the vapours formed during the process are condensed on the cooled surfaces inside the distillation unit thus allowing very short residence times, which is important especially in cases where the valuable substances are thermally instable. On the other hand, if the condenser is outside the heated surfaces of the distillation thin film chamber, there is the possibility to use a fractionation column during the distillation process and hence obtain sharper and better separation between light and heavier components.

In this embodiment (A) when using tall oil pitch as source material the separation of the light fraction (A1) can take place by using 140–230° C. distillation temperature and from about 0.01 to 10 mbar vacuum pressure. More preferably the distillation conditions are, for example, 200° C. at the heated surface and up to 2–3 mbar pressure. The obtained distillate contains light terpenic compounds, wax alcohols (C20–C28 saturated alcohols), stilbenes, transesterified esters and possible liberated free acids. It is possible to separate the wax alcohols from the distillate by using e.g. solvent crystallisation.

The most part of the valuable sterols remain in the residue, from which they can be separated either by (A2) applying different solvent crystallisation and filtration techniques directly, or in most typical cases, more preferably (A3) after an additional high vacuum thin film or short path distillation step where the fraction containing valuable substances is separated from the least volatile fraction including e.g. inorganic salts by evaporating the valuable substances. The functioning conditions in evaporation of sterols can be e.g. vacuum from about 0.01 mbar to about 10 mbar; and temperature of the film in the heated surface of the distillation unit between 200 and 300° C. More preferable conditions are e.g. evaporation temperature 250–280° C. at 0.01–1 mbar vacuum.

In another embodiment (B) the volatile components are evaporated from the dried transesterified material by using as high vacuum as possible and high distillation temperatures, whereby the valuable substances are distilled over. After evaporation the valuable substances are separated from the distillate by using other separation techniques or evaporative fractionation is continued by distilling the light fraction from the first distillate by using similar conditions as in A1. Then the separation of the valuable substances can take place as in A2 or A3.

After the evaporation fractionation the valuable substances can be isolated from the fractions by e.g. crystallisation from suitable solvents or solvent mixtures according to any known process.

A preferred embodiment of the invention is to use tall oil pitch as tall oil based source material. It is also preferred to use an alkali hydroxide for the conversion, dry the mixture and perform the transesterification with an alkali metal alkoxide. Another preferred embodiment is to use an alkali metal alkoxide for both the conversion and the transesterification. Acidulation of the salts after the transesterification seems also to be a preferred way of realising the invention, and optionally the so obtained free fatty acids can still be esterified with an alcohol before the evaporative fractionation.

The following examples are intended to illustrate the invention.

EXAMPLE 1

Conversion of Free Acids in Tall Oil Pitch to Salts Using NaOH, Drying and Transesterification of the Mixture Tall oil pitch (acid value 17 mg KOH/g, saponification value 91 mg KOH/g, total sterol content 10.3 weight-%, free sterols 3.1 w-%) was used as starting material. The free acids of the pitch were converted to salts by mixing carefully 8.0 g of 50% NaOH solution into 300 g of pitch at 80° C. The moisture was evaporated in vacuum at 100° C. for two hours in a rotavapor. The mixture was transferred into an autoclave and 1.3 g NaOMe in 280 g methanol was added. The mixture was then heated up to 160° C. carefully mixing. The reaction rate was checked by analysing samples taken as a function of reaction time. After 3 hours reaction time the sample was dried in a rotavapor. The sterol content of a neutralised (added an equivalent molar amount of acetic acid to the amount of catalyst present in the sample) sample according to GC analysis was 9.8 w-%. However, already after an hour reaction the sterol content was 9.1 w-%. The result indicates that the reaction proceeded almost into completion within 1–2 hours reaction and practically all of the sterol esters were transesterified.

EXAMPLE 2

Conversion of Free Acids to Salts and Transesterfication of Tall Oil Pitch Using NaOMe 300 g tall oil pitch (the same as in example 1) and 7.5 g sodium methoxide in 360 g MeOH was put into an autoclave. The temperature was raised to 150° C. (pressure ~10 bar) and mixing was continued for three hours. Remaining MeOH was removed with a rotavapor. The dried reaction mixture contained 9.8 w-% free sterols.

EXAMPLE 3

Conversion of Free Fatty Acids in Tall Oil Pitch to Salts Using CaO and Transesterification Using NaOMe 300 g tall oil pitch (the same as in example 1) and 6 g CaO in 200 g MeOH was put into an autoclave and mixed for 1 hour at 50° C. Thereafter 2.5 g of NaOMe in 100 g of methanol was added and the temperature was raised to 160° C. Mixing was continued for 3 hours, whereafter the reaction mixture was cooled and neutralised with 10% sulphuric acid to destroy the catalyst. The reaction mixture separated into two phases, probably due to formation of insoluble fatty acid calcium salts. The solvent was evaporated in a rotavapor. The free sterol content of the dry product was 8.7 w-%.

EXAMPLE 4

Evaporative Fractionation of Transesterified Tall Oil Pitch

For the evaporative fractionation of transesterified pitch a bigger amount of raw material was prepared by using the procedure applied in example 2. The free sterol content of this batch was 9.7 w-%. The equipment used for the evaporation fractionation trials was the laboratory unit KDL 5 manufactured by UIC, Alzenau, Germany.

a) Evaporation of Light Fraction

The material was fed into the distillation unit at 100° C. Feed rate was 15 ml/min and condenser temperature 60° C. The temperature of the heating oil was 200° C. and the vacuum about 1 mbar. 30 of the mass was distillated over and the sterol content of this fraction, mainly consisting of fatty acid methyl esters and light b) Evaporation of Sterol Fraction from the Residue The residue was heated to 120° C. and fed again to the distillation unit. Feed rate was 10 ml/min, heating oil temperature 280° C. and the temperature of the condenser 100° C. A light coloured distillate was obtained. This distillate—the amount of which was estimated to be clearly over 50%—contained 26.2 w-% free sterols. The sterol content of the black viscous residue was 1.3 w-%.

EXAMPLE 5

Isolation of Wax Alcohols from the Light Distillate 50 g of heptane was added into 50 g of the light fraction obtained in example 4. The mixture was heated until all the solid material formed during storage of the matter was dissolved. Upon cooling to 10° C. a white crystalline precipitate was formed. The precipitate was separated by filtration, washed with a small amount of heptane, dried and analysed. The precipitate consisted of an almost pure mixture of $C_{20}$–$C_{26}$ wax alcohols.

EXAMPLE 6

Isolation of Sterols from Distillates 10 g of the sterol fraction obtained in example 4 was dissolved in 20 g of solvent, which consisted of methyl ethyl ketone, methanol and water (70:20:10), by refluxing. After cooling to room temperature a white crystalline precipitate was formed. The precipitate was filtered, washed with a small amount of the solvent and dried. The amount of crystals recovered was 2.3 g and the sterol content 94 w-%.

The invention claimed is:

1. A process for recovering sterols and/or wax alcohols from a crude tall oil based source material comprising sterols and/or wax alcohols in esterified from and fatty and/or rosin acids and optionally sterols and/or wax alcohols in free form, said method comprising the steps of:
   a) converting free acids in the source material to corresponding salts,
   b) removing water is present, c) transesterifying the esterified sterols and/or wax alcohols present in the dry material obtained in step a or step b with an alcohol reagent to liberate sterols and/or wax alcohols,
d) evaporative fractioning the transesterified material, and
e) isolating sterols and/or wax alcohols from the obtained fraction(s) and/or the residue.

2. The process according to claim 1, wherein the conversion step is performed using an oxide, hydroxide or alkoxide of an alkali metal or alkaline earth metal.

3. The process according to claim 1, wherein the transesterification step c is performed using as catalyst an alkoxide or hydroxide of an alkali metal.

4. The process according to claim 1, wherein the transesterification step c is performed using a lower alcohol as alcohol reagent.

5. The process according to claim 1 wherein the transesterification step c is performed using a high boiling polyhydric alcohol as alcohol reagent.

6. The process according to claim 1, wherein the fractionation step d includes the steps of
   d1) evaporation of excess of lower alcohol reagent partly or completely, and
   d2) evaporation fractionation of the transesterified material.

7. The process according to claim 1, wherein after transesterification step c the organic salts formed during conversion step a are completely or partially acidulated to corresponding acids before performing fractionation step d.

8. The process according to claim 1, wherein free acids present in the source material are partially esterified before performing conversion step a.

9. The process according to claim 8 wherein the esterification is performed using a lower alcohol or a high boiling polyhydric alcohol as alcohol reagent.

10. The process according to claim 1 wherein step a and step c are performed in the same stage under anhydrous conditions using an alkoxide of an alkali metal or alkaline earth metal such as sodium methoxide as reagent in the conversion step a and as catalyst in the transesterification step c.

11. The process according to claim 5, wherein the high boiling polyhydric alcohol is selected from the group consisting of ethylene glycol, propylene glycol, and glycerol of diethylene glycol.

12. The process according to claim 9, wherein the high boiling polyhydric alcohol is selected from the group consisting of ethylene glycol, propylene glycol, and glycerol of diethylene glycol.

13. The process according to claim 10, wherein the alkoxide of an alkali metal or alkaline earth metal is sodium methoxide.

* * * * *